(12) United States Patent
Biedermann et al.

(10) Patent No.: US 9,066,759 B2
(45) Date of Patent: Jun. 30, 2015

(54) RECEIVING PART FOR RECEIVING A ROD FOR COUPLING THE ROD TO A BONE ANCHORING ELEMENT AND A BONE ANCHORING DEVICE

(75) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 186 days.

(21) Appl. No.: 13/323,433

(22) Filed: Dec. 12, 2011

(65) Prior Publication Data

US 2012/0179209 A1     Jul. 12, 2012

Related U.S. Application Data

(60) Provisional application No. 61/421,959, filed on Dec. 10, 2010.

(30) Foreign Application Priority Data

Dec. 10, 2010    (EP) ..................................... 10194596

(51) Int. Cl.
*A61B 17/70*        (2006.01)
(52) U.S. Cl.
CPC .................................. *A61B 17/7037* (2013.01)
(58) Field of Classification Search
CPC ........... A61B 17/7001; A61B 17/7032; A61B 17/7034; A61B 17/7035; A61B 17/7037; A61B 17/7038; A61B 17/704; A61B 17/7041; A61B 17/7043; A61B 17/7044; A61B 17/7046; A61B 17/844; A61B 17/8685
USPC .............. 606/53, 60, 246–279, 300–320, 328
See application file for complete search history.

(56) References Cited

U.S. PATENT DOCUMENTS 5,584,834 A * 12/1996 Errico et al. ................... 606/264
5,586,984 A * 12/1996 Errico et al. ................... 606/264

(Continued)

FOREIGN PATENT DOCUMENTS

| EP | 2 204 129 A1 | 7/2010 |
|---|---|---|
| WO | WO 2004/089245 A2 | 10/2004 |
| WO | WO 2007/038350 A2 | 4/2007 |

OTHER PUBLICATIONS

European Search Report for European Application No. 10 194 596.2, European Search Report dated Mar. 22, 2011 and mailed Apr. 1, 2011 (6 pgs.).

*Primary Examiner* — Pedro Philogene
*Assistant Examiner* — Lynnsy Summitt
(74) *Attorney, Agent, or Firm* — Christie, Parker & Hale, LLP

(57) ABSTRACT

A receiving part for coupling a rod to a bone anchoring element includes: a receiving part body with a rod receiving portion and a head receiving portion having an open end for introducing a head of a bone anchoring element, and a locking ring, wherein the head receiving portion includes a plurality of flexible wall portions, the flexible wall portions and the locking ring being configured to engage each other at circumferentially distinct pressure areas having positions corresponding to circumferentially separated projections on at least one of the flexible wall portions or the locking ring, and wherein the locking ring exerts a first force on at least one of the flexible wall portions at a corresponding pressure area, and exerts a second force less than the first force on the at least one flexible wall portion in a region circumferentially adjacent to the corresponding pressure area.

21 Claims, 12 Drawing Sheets

(56) References Cited

U.S. PATENT DOCUMENTS

| | | | | |
|---|---|---|---|---|
| 5,683,392 A | * | 11/1997 | Richelsoph et al. | 606/272 |
| 5,688,274 A | * | 11/1997 | Errico et al. | 606/276 |
| 5,733,285 A | * | 3/1998 | Errico et al. | 606/278 |
| 6,053,917 A | * | 4/2000 | Sherman et al. | 606/270 |
| 6,254,602 B1 | * | 7/2001 | Justis | 606/272 |
| 6,287,311 B1 | * | 9/2001 | Sherman et al. | 606/78 |
| 6,582,436 B2 | * | 6/2003 | Schlapfer et al. | 606/266 |
| 7,022,122 B2 | * | 4/2006 | Amrein et al. | 606/266 |
| 7,090,674 B2 | * | 8/2006 | Doubler et al. | 606/277 |
| 7,306,603 B2 | * | 12/2007 | Boehm et al. | 606/279 |
| 7,850,715 B2 | * | 12/2010 | Banouskou et al. | 606/246 |
| 7,988,694 B2 | * | 8/2011 | Barrus et al. | 606/86 A |
| 8,021,398 B2 | * | 9/2011 | Sweeney et al. | 606/269 |
| RE42,867 E | * | 10/2011 | Hammill et al. | 606/277 |
| 8,100,948 B2 | * | 1/2012 | Ensign et al. | 606/267 |
| 8,162,991 B2 | * | 4/2012 | Strauss et al. | 606/269 |
| 8,167,910 B2 | * | 5/2012 | Nilsson | 606/264 |
| 8,192,470 B2 | * | 6/2012 | Biedermann et al. | 606/265 |
| 8,197,519 B2 | * | 6/2012 | Schlaepfer et al. | 606/278 |
| 8,267,969 B2 | * | 9/2012 | Altarac et al. | 606/269 |
| 8,328,817 B2 | * | 12/2012 | Strauss | 606/102 |
| 8,361,122 B2 | * | 1/2013 | Barrus et al. | 606/267 |
| 2001/0047173 A1 | | 11/2001 | Schlapfer et al. | |
| 2002/0032443 A1 | | 3/2002 | Sherman et al. | |
| 2005/0080415 A1 | * | 4/2005 | Keyer et al. | 606/61 |
| 2006/0149244 A1 | * | 7/2006 | Amrein et al. | 606/61 |
| 2006/0200128 A1 | * | 9/2006 | Mueller | 606/61 |
| 2008/0183215 A1 | * | 7/2008 | Altarac et al. | 606/265 |
| 2008/0312701 A1 | * | 12/2008 | Butters et al. | 606/305 |
| 2010/0160975 A1 | * | 6/2010 | Biedermann et al. | 606/302 |
| 2010/0160977 A1 | * | 6/2010 | Gephart et al. | 606/305 |
| 2010/0168800 A1 | * | 7/2010 | Biedermann et al. | 606/302 |
| 2010/0168801 A1 | * | 7/2010 | Biedermann et al. | 606/302 |
| 2010/0204735 A1 | * | 8/2010 | Gephart et al. | 606/264 |
| 2010/0234902 A1 | * | 9/2010 | Biedermann et al. | 606/305 |
| 2010/0262196 A1 | * | 10/2010 | Barrus et al. | 606/308 |
| 2011/0046683 A1 | * | 2/2011 | Biedermann et al. | 606/305 |
| 2011/0276098 A1 | * | 11/2011 | Biedermann et al. | 606/305 |
| 2012/0041490 A1 | * | 2/2012 | Jacob et al. | 606/264 |
| 2012/0095516 A1 | * | 4/2012 | Dikeman | 606/305 |
| 2012/0165874 A1 | * | 6/2012 | Biedermann et al. | 606/278 |
| 2012/0172932 A1 | * | 7/2012 | Biedermann et al. | 606/279 |
| 2012/0179209 A1 | * | 7/2012 | Biedermann et al. | 606/305 |
| 2012/0179211 A1 | * | 7/2012 | Biedermann et al. | 606/328 |
| 2012/0209335 A1 | * | 8/2012 | Termyna et al. | 606/300 |

* cited by examiner

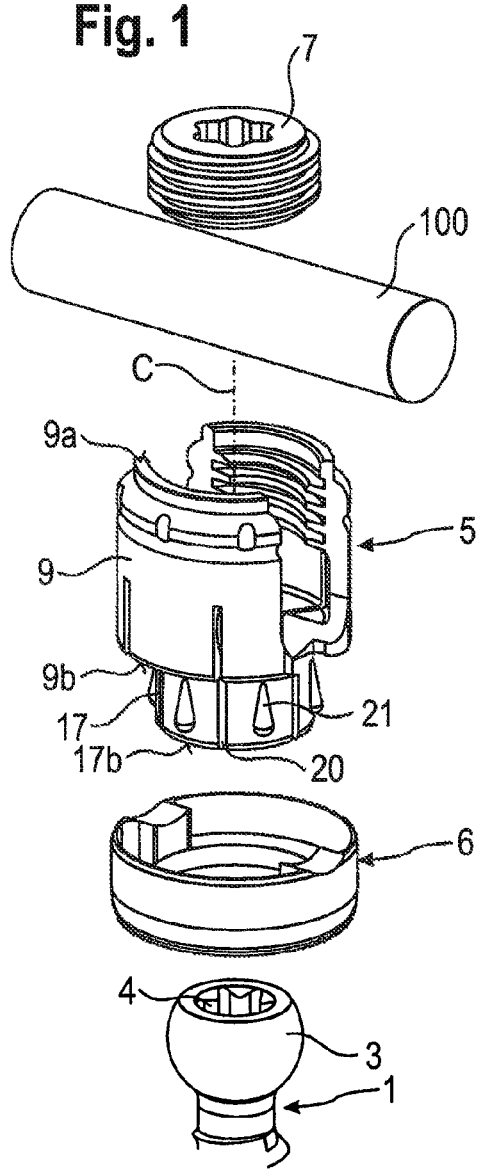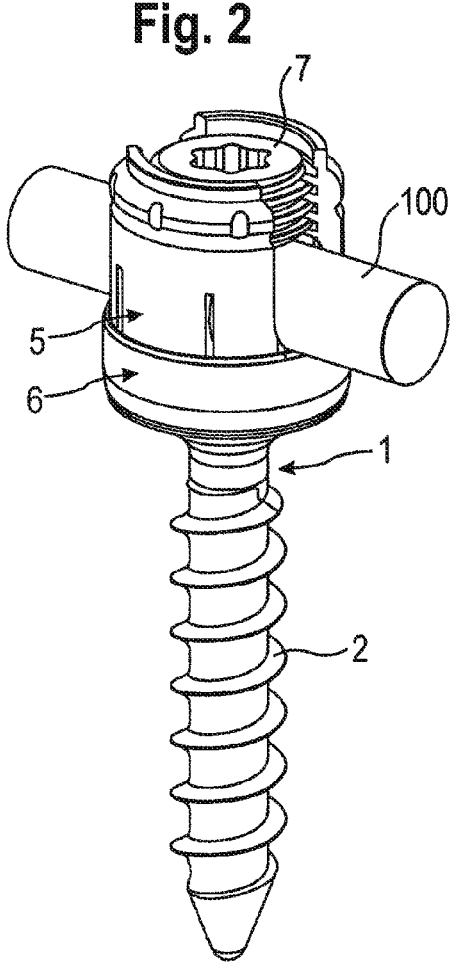

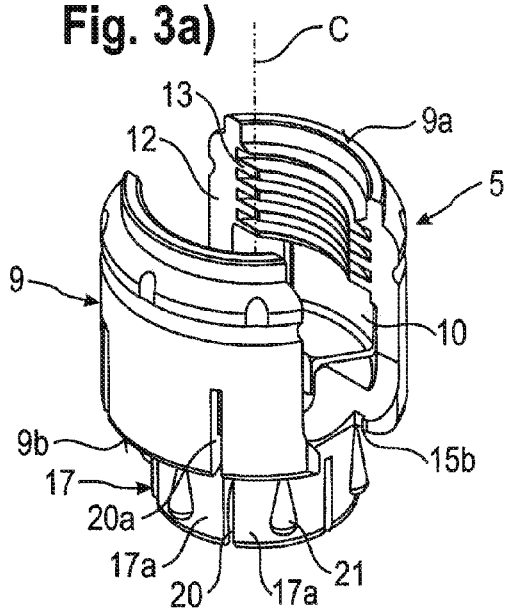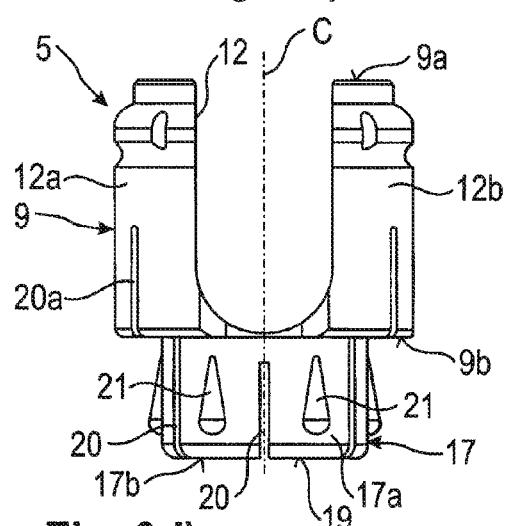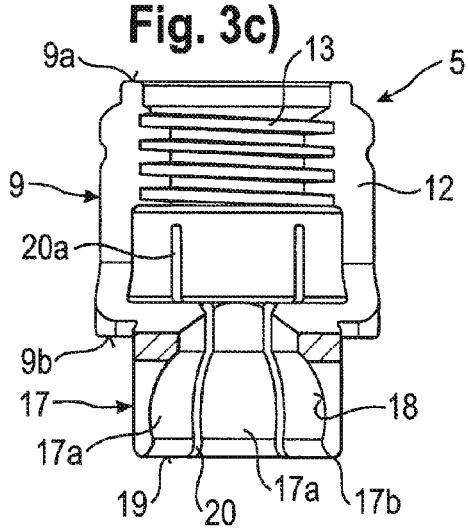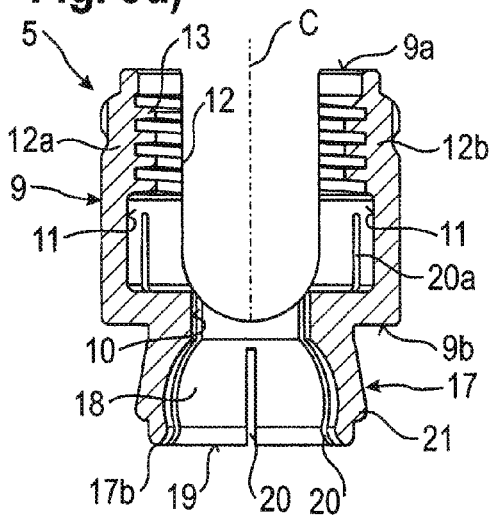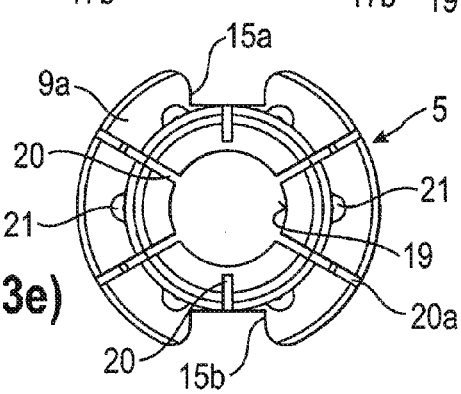

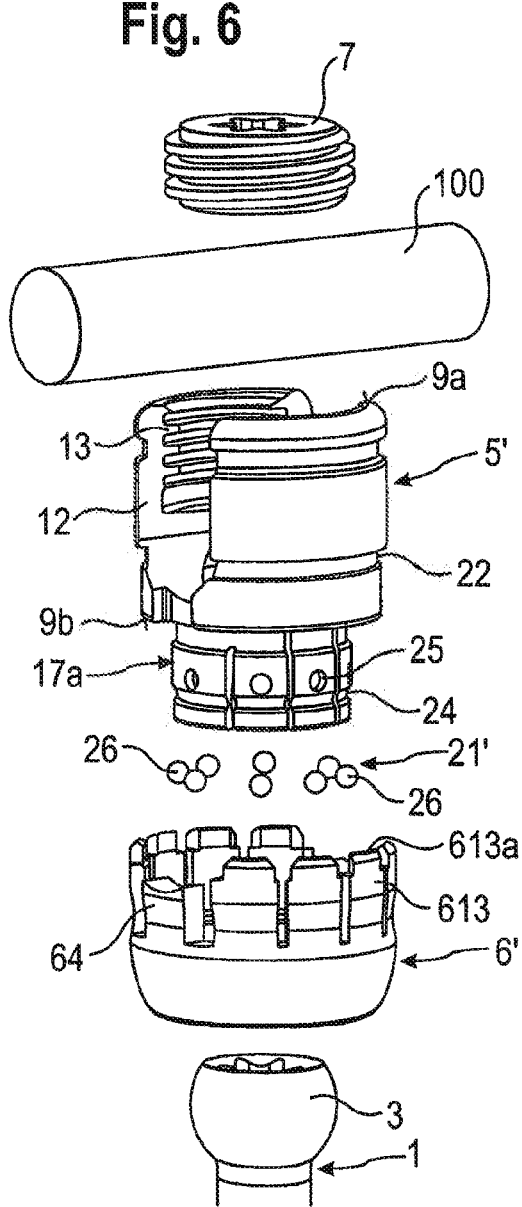
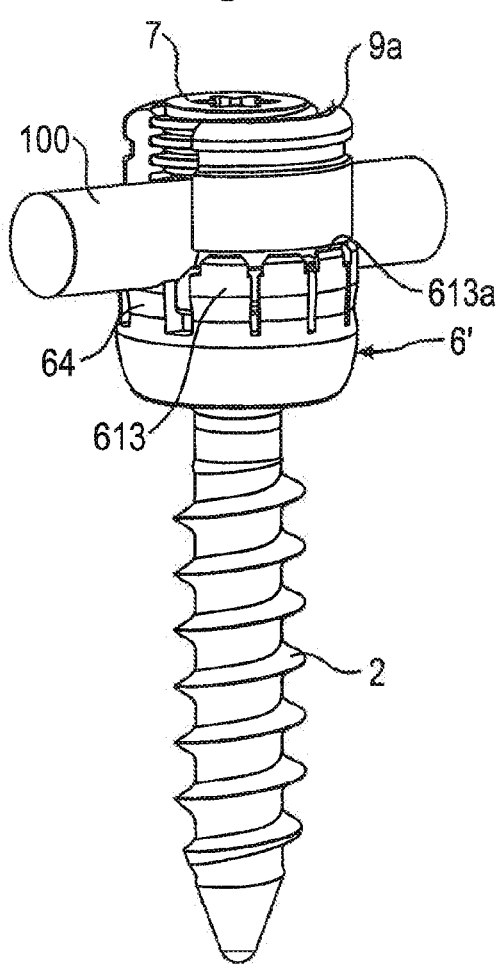

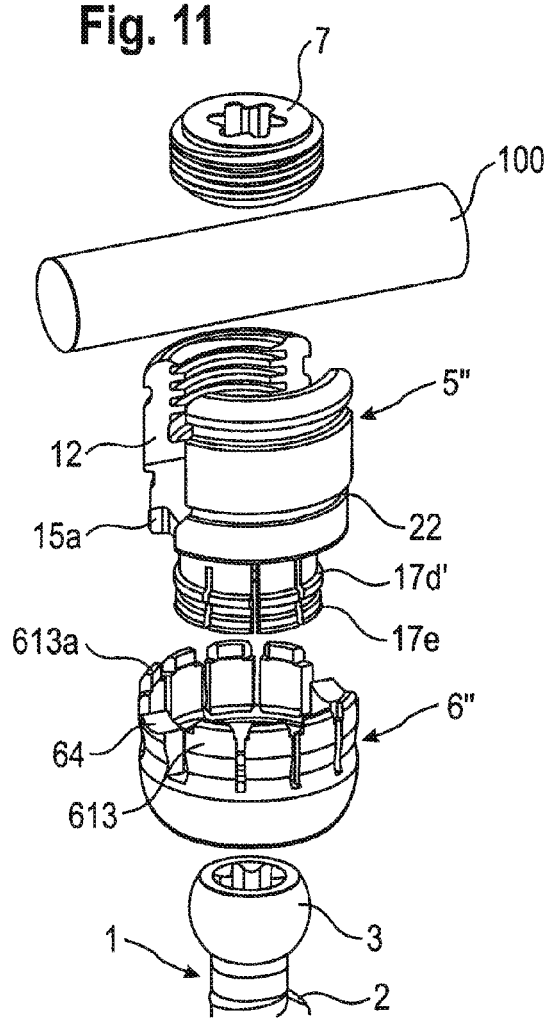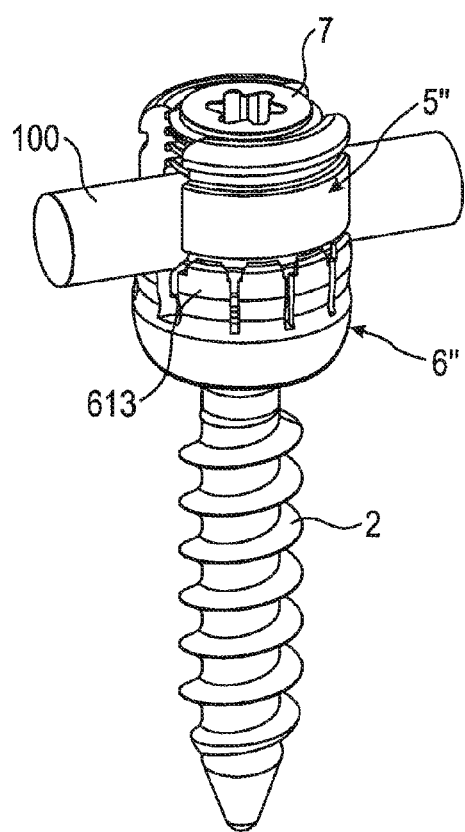

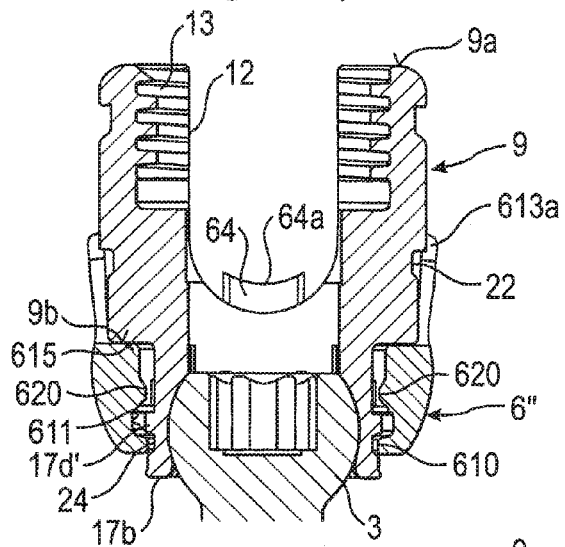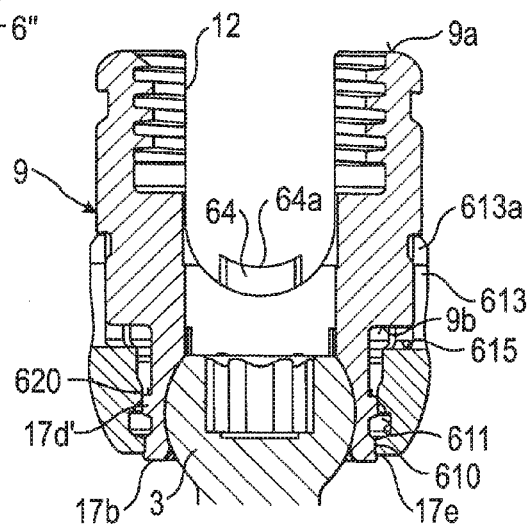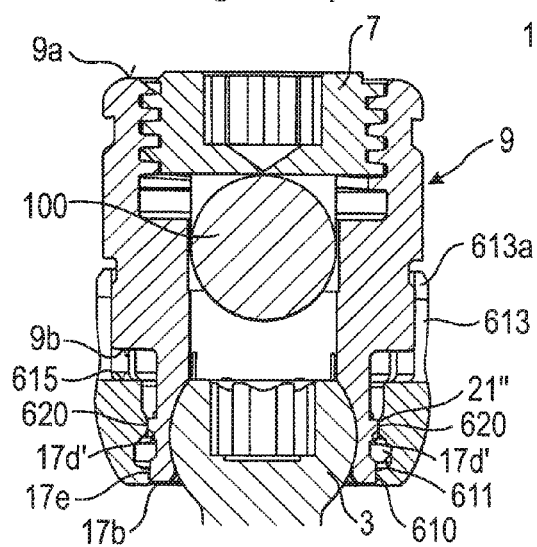

RECEIVING PART FOR RECEIVING A ROD FOR COUPLING THE ROD TO A BONE ANCHORING ELEMENT AND A BONE ANCHORING DEVICE

CROSS-REFERENCE TO RELATED APPLICATION

The present application claims the benefit of U.S. Provisional Patent Application Ser. No. 61/421,959, filed Dec. 10, 2010, the contents of which are hereby incorporated by reference in their entirety, and claims priority to European Patent Application EP 10 194 596.2, filed Dec. 10, 2010, the contents of which are hereby incorporated by reference in their entirety.

BACKGROUND

1. Field of the Invention

The invention relates to a receiving part for receiving a rod for coupling the rod to a bone anchoring element, and a bone anchoring device with such a receiving part. The receiving part includes a receiving part body with a rod receiving portion and a head receiving portion for receiving the head of the bone anchoring element and a locking ring for locking the head in the head receiving portion. The head can be clamped by compressing a plurality of flexible wall sections with the locking ring, where the clamping force is generated in a wall section at a circumferentially distinct pressure area.

2. Description of Related Art

U.S. Pat. No. 5,733,285 describes a polyaxial colletted locking mechanism for use with an orthopaedic apparatus including a screw having a curvate head and a coupling element. The coupling element has a tapered and colletted portion having an interior chamber in which the curvate head is initially polyaxially disposed. A locking collar is disposed around the tapered and colletted portion such that translation thereof in the direction of the expanding taper causes the interior volume to contract onto the curvate head and lock it therein.

WO 2007/038350 A2 discloses an apparatus for connecting a bone anchor to a support rod, the apparatus including a connector body and a cap. The connector body has a socket for insertion, angulation and removal of a bone anchor. A sleeve is provided which is configured to fit over the connector body for locking the bone anchor in the socket.

SUMMARY

It is an object of the invention to provide an improved receiving part for receiving a rod for coupling the rod to a bone anchoring element, and a bone anchoring device with such a receiving part, which allows for safe handling during surgery and safe fixation of the bone anchoring element and the rod.

A receiving part according to embodiments of the invention is improved with respect to clamping and locking of a head of a bone anchoring element. Exerting pressure by the locking ring at positions where a head receiving portion has slits may not contribute to an effective clamping of the head. Therefore, the bone anchoring device according to embodiments of the present invention is designed such that the pressure force exerted by the locking ring onto the head receiving portion is concentrated at distinct pressure areas separated from each other in a circumferential direction. Hence, the clamping force can be precisely applied, which improves the safety of the fixation.

Furthermore, the receiving part according to embodiments of the invention can have a pre-locking function, where the locking ring is latched with respect to the receiving part body in a position in which the head is inserted but is not yet locked, so that the head is prevented from removal from the receiving part.

With the bone anchoring device according to embodiments of the invention, a modular system can be provided that allows for combining various anchoring elements with any suitable receiving part on demand, depending on the specific clinical requirements. This reduces the costs associated with polyaxial screws, reduces inventory, and gives a surgeon a substantial or wider choice of implants.

BRIEF DESCRIPTION OF THE DRAWINGS

Further features and advantages of the invention will become apparent from the description of exemplary embodiments by means of the accompanying drawings. In the drawings:

FIG. 1 shows a perspective exploded view of a first embodiment of the bone anchoring device;

FIG. 2 shows a perspective view of the bone anchoring device of FIG. 1 in an assembled state;

FIGS. 3a to 3e show a perspective view, a side view, a first cross-sectional view, a second cross-sectional view, and a bottom view, respectively, of a receiving part body of the bone anchoring device according to the first embodiment;

FIG. 6 shows a perspective exploded view of a second embodiment of the bone anchoring device;

FIG. 7 shows a perspective view of the bone anchoring device of FIG. 6 in an assembled state;

FIG. 11 shows a perspective exploded view of a third embodiment of the bone anchoring device;

FIG. 12 shows a perspective view of the bone anchoring device of FIG. 11 in an assembled state;

FIGS. 15a to 15c show cross-sectional views of different steps of use of the bone anchoring device according to the third embodiment.

DETAILED DESCRIPTION

Figure 4A:
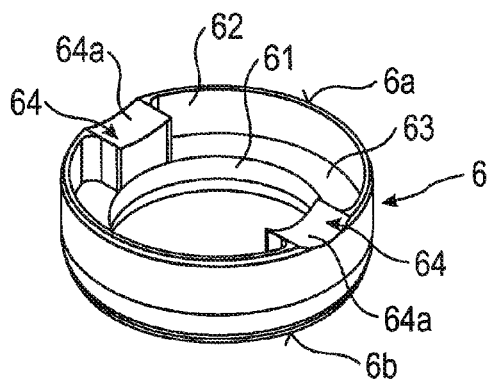
FIGS. 4a to 4d show a perspective view, a side view, a bottom view, and a cross-sectional view, respectively, of a locking ring of the bone anchoring device according to the first embodiment.
Figure 4B:
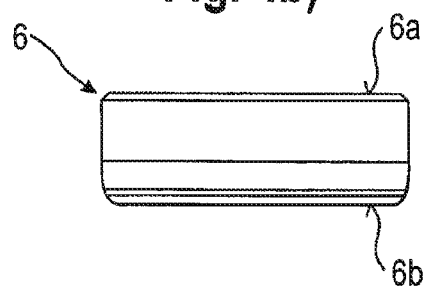
Figure 4C:
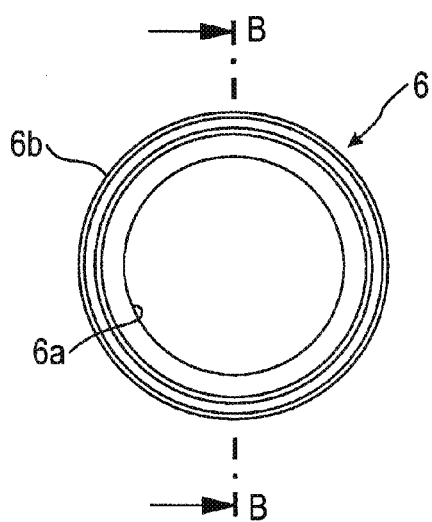
Figure 4D:
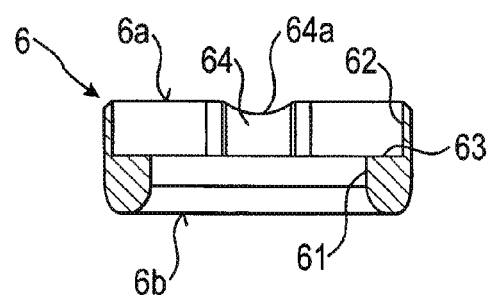

A first embodiment of a bone anchoring device is shown in FIGS. 1 to 5c. The bone anchoring device includes a bone anchoring element 1 in the form of a bone screw having a threaded shaft 2 and a head 3 with a spherically-shaped outer surface portion. The head 3 has a recess 4 for engagement with a driver or tool. The bone anchoring device further includes a. receiving part body 5 for receiving a rod 100 to connect the rod 100 to the bone anchoring element 1. For locking the head 3 in the receiving part body 5, a locking ring 6 is provided that engages the receiving part body 5. Furthermore, a fixation device in the form of; for example, an inner screw 7 is provided for fixing the rod 100 in the receiving part body 5.

FIG. 3c is a cross-sectional view where the section is being taken in a plane containing a rod axis, and FIG. 3d is a cross-sectional view where the section is taken perpendicular to the rod axis. As shown in particular in FIGS. 1 to 3e, the receiving part body 5 includes a rod receiving portion 9 which is substantially cylindrical and has a first end 9a and a second end 9b opposite the first end 9a, and a central axis or cylinder axis C. A coaxial first bore 10 is provided at the second end 9b. A diameter of the first bore 10 is smaller than a diameter of the head 3 of the bone anchoring element 1. A coaxial second bore 11 extends from the first end 9a to a distance from the second end 9b. A diameter of the second bore 11 is greater than that of the first bore 10. A substantially U-shaped recess 12 extends in the rod receiving portion 9 from the first end 9a in the direction of the second end 9b, a diameter of the recess 12 being slightly larger than a diameter of the rod 100 to allow for placing of the rod 100 in the recess 12 and for guiding the rod 100 therein. By means of the recess 12 two free legs 12a, 12b are formed, on which an internal thread 13 is provided. The internal thread 13 can be a metric thread, flat thread, a negative angle thread, a saw-tooth thread, or any other thread form. If the fixation device is in the form of the inner screw 7, a thread form such as a flat thread or a negative angle thread can be used which prevents or reduces splaying of the legs 12a, 12b when the inner screw 7 is tightened. A depth of the recess 12 is such that the rod 100 and the inner screw 7 can be inserted between the legs 12a, 12b. It shall be noted that the diameter of the coaxial bore 11 can vary along the central axis C.

As can be seen in particular in FIGS. 3a and 3e cut-outs 15a, 15b are provided in the rod receiving portion 9 on either end of the channel formed by the recess 12.

At the side of the second end 9b, the receiving part body 5 further includes a head receiving portion 17 providing an accommodation space for the head 3 of the bone anchoring element 1. The head receiving portion 17 is substantially cylindrically-shaped, with an outer diameter which may be smaller than a greatest outer diameter of the rod receiving portion 9, such that the head receiving portion 17 may be recessed with respect to the rod receiving portion 9, as can be best seen, for example, in FIGS. 3b and 3c. An internal hollow section 18 in the head receiving portion 17 forms a seat for the head 3 of the bone anchoring element 1. The hollow section 18 is open via the opening 19 to a free end 17b of the head receiving portion 17. In the embodiment shown, the hollow section 18 is spherically shaped to accommodate the spherical head 3. However, the hollow section 18 generally may be adapted to any other shape of the head 3, or can be shaped otherwise so as to allow locking of the head 3 in the head receiving portion 17.

A plurality of slits 20 are provided in the head receiving portion 17. The slits 20 extend from the free end 17b to a distance from the second end 9b of the rod receiving portion 9. Generally, the slits 20 extend over a region which includes a largest inner diameter of the hollow section 18. The slits 20 render the head receiving portion 17 flexible, so that the head receiving portion 17 can be compressed to clamp and finally lock the head 3 in the internal hollow section 18 by friction. The head receiving portion 17 is configured to allow the insertion of the head 3 by expanding the head receiving portion 17, and to clamp and finally lock the head 3 by compressing the head receiving portion 17. Some of the slits 20 extend further, for example, into the rod receiving portion 9, forming slits 20a as shown, for example, in FIGS. 3a and 3b. By means of this, the insertion of the head 3 can be further facilitated.

By way of the slits 20, 20a, flexible wall sections 17a of the head receiving portion 17 are formed. On each of the flexible wall sections 17a, a pressure area is formed in which pressure generated by cooperation of the locking ring 6 with the head receiving portion 17 is applied to the head 3. The pressure area is a distinct area seen in a circumferential direction within the flexible wall sections 17a. In the first embodiment, the pressure area is formed by a teardrop-shaped projection 21 at the outer surface of each flexible wall section 17a. The teardrop-shaped projection 21 is arranged at a center of a corresponding flexible wall section 17a in an axial direction and in a circumferential direction. The teardrop-shaped projection 21 is oriented such that its height and width increases towards the free end 17b. By means of this, an outer diameter of the head receiving portion increases towards the free end 17b in regions of the teardrop-shaped projections, as can be seen best in FIG. 3d. Hence, an outwardly tapered pressure area is provided at each of the flexible wall sections 17a.

The locking ring 6 will now be described with reference to FIGS. 4a to 4d. FIG. 4a shows a perspective view of the locking ring 6. The locking ring 6 is substantially cylindrical and has an upper end 6a and a lower end 6b. In a mounted state, the upper end 6a is oriented closer to the first end 9a of the rod receiving portion 9, and the lower end 6b is oriented towards the free end 17b of the head receiving portion 17. Adjacent the lower end 6b, the locking ring 6 is substantially hollow with a bore having a cylindrically-shaped inner cylindrical surface 61, a diameter of which is slightly smaller than the outer diameter of the head receiving portion 17 in the regions of the outermost areas of the teardrop-shaped projections 21. By means of this, the head receiving portion 17 can be compressed to clamp and to finally lock the head 3 when the locking ring 6 is around the head receiving portion 17 in a locking position. The lower end 6b of the locking ring 6 may have a rounded edge as shown, for example, in FIG. 4d, which shows a cross-sectional view of the locking ring 6 along line B-B of FIG. 4c. Adjacent the cylindrical surface 61, the locking ring 6 has a circular rim 62 including the upper end 6a. Between the circular rim 62 and the hollow cylindrical surface 61 an annular abutment surface 63 is formed. A height of the circular rim 62 is such that when the locking ring 6 is in its lowermost position with respect to the receiving part 5, the rim 62 bridges the gap between the abutment surface 63 and the second end 9b, as shown, in particular in FIG. 5b. This may serve, for example, for preventing tissue growing into the gap between the abutment surface 63 of the locking ring 6 and the second end 9b of the receiving part 9. The locking ring 6 further has two projections 64, as shown in particular in FIG. 4a and FIG. 4d which project from the abutment surface 63 towards the upper end 6a. The projections 64 are offset from each other by 180° and may have a concave upper surface 64a for facilitating receiving the rod 100.

All parts of the bone anchoring device may be made of a bio-compatible material, for example, of titanium or stainless steel, or of a bio-compatible alloy, such as Nitinol, or of a bio-compatible plastic material such as, for example, polyetheretherketone (PEEK). The parts can all be made of the same or of different materials.

Figure 5A:
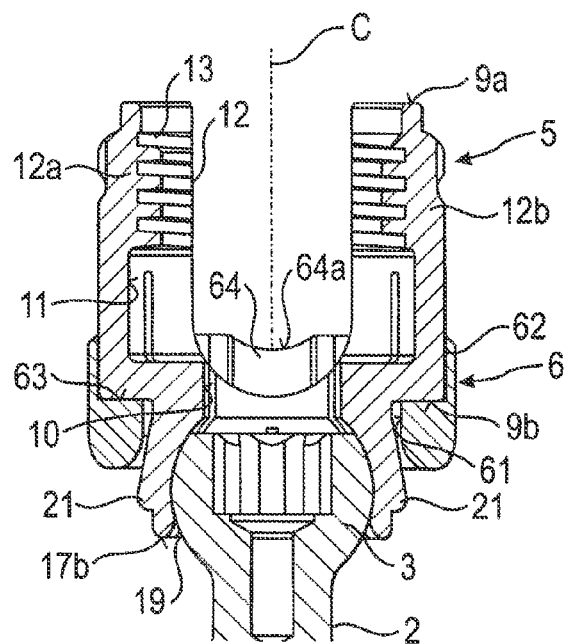
FIGS. 5a to 5c show cross-sectional views of steps of use of the bone anchoring device according to the first embodiment.
Figure 5B:
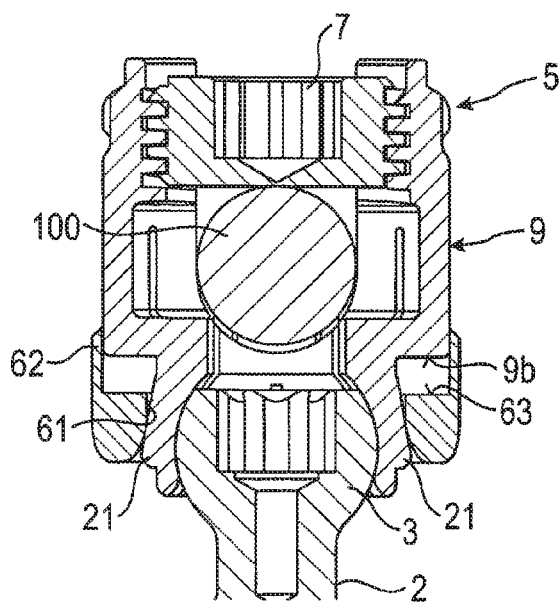

The assembly and use of the bone anchoring device will now be explained with reference to FIGS. 5a to 5c. The locking ring 6 is mounted from the free end 17b of the head receiving portion 17 by compressing the flexible wall sections 17a. The locking ring 6 is moved into a first position, which is an insertion position, shown in FIG. 5a. In this position, the annular abutment surface 63 of the locking ring 6 abuts against the lower end 9b of the rod receiving portion 9. Between the inner cylindrical surface 61 and the outer surface of the head receiving portion 17, there is a gap which allows the expansion of the flexible wall sections 17a to some extent. In this condition, the head 3 can be inserted from the free end 17b by expanding the hollow internal section 18. Once the head 3 is inserted into the hollow internal section 18, the locking ring 6 is prevented from falling out, since the outer diameter of the head receiving portion 17 in the area of the highest point of the teardrop-shaped projections 21 is larger than the inner diameter of the cylindrical surface 61. The projections 64 of the locking ring are aligned with the U-shaped recess 12. As can be seen in FIG. 5a, in this first position, the projections 64 project above a bottom of the U-shaped recess 12.

In this condition, between the receiving part body 5, the locking ring 6 and the anchoring element 1, which in some embodiments may be preassembled, the anchoring element 1 can be inserted into a bone part or a vertebra. The recess 4 of the head can be accessed with a driver or tool through the first bore 10. In the condition shown in FIG. 5a, the receiving part 5 is still pivotable relative to the head 3 of the bone anchoring element 1. Usually, at least two bone anchoring devices are used and are connected to a stabilization rod 100. After insertion of each of the bone anchoring devices, the receiving part bodies 5 are rotated and/or pivoted to be adjusted to receive the rod 100. Once a correct or desired position of the bone anchoring devices with respect to the rod is achieved, the inner screw 7 is screwed between the legs 12a, 12b of each bone anchoring device until it presses onto the rod 100. The rod 100 is thereby shifted towards the bottom of the U-shaped recess 12, thereby engaging the upper surface 64a of the projections 64 and shifting the locking ring 6 down (e.g., towards the free end 17b).

When the locking ring 6 is shifted towards the free end 17b of the head receiving portion 17, the cylindrical inner surface 61 engages the outwardly tapering surfaces of the teardrop-shaped projections 21, thereby creating an increasing pressure onto the flexible wall sections 17a. When the locking ring 6 has been fully moved downwards, the pressure exerted by the locking ring 6 onto the flexible wall sections 17a is such that the head 3 is finally locked in the hollow internal section 18.

Figure 5C:
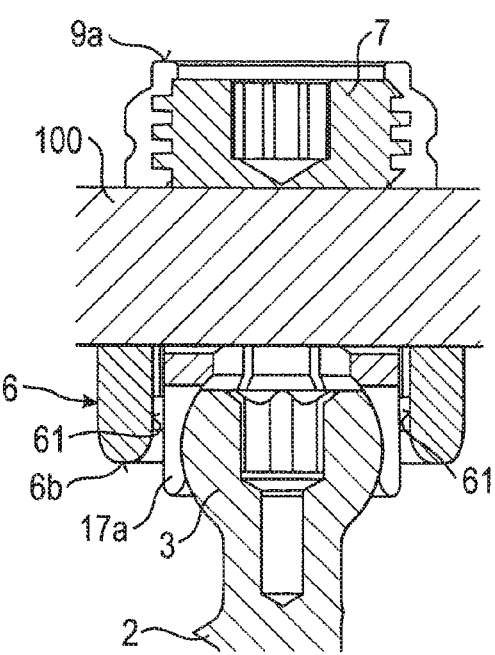
Figure 8A:
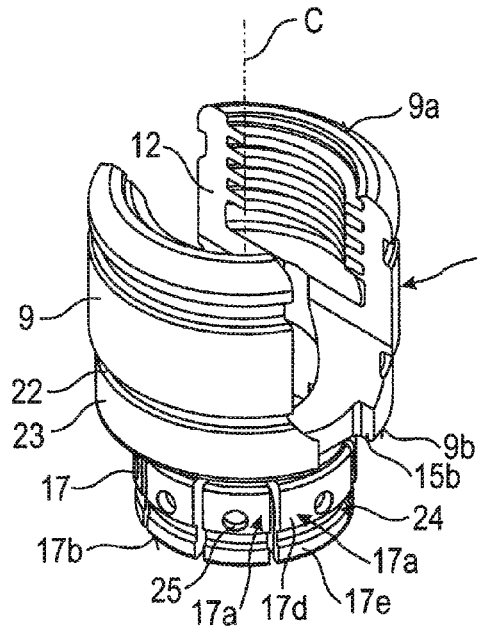
FIGS. 8a to 8d show a perspective view, a side view, a cross-sectional view, and a bottom view, respectively, of a receiving part body of the bone anchoring device of the second embodiment.
Figure 8B:
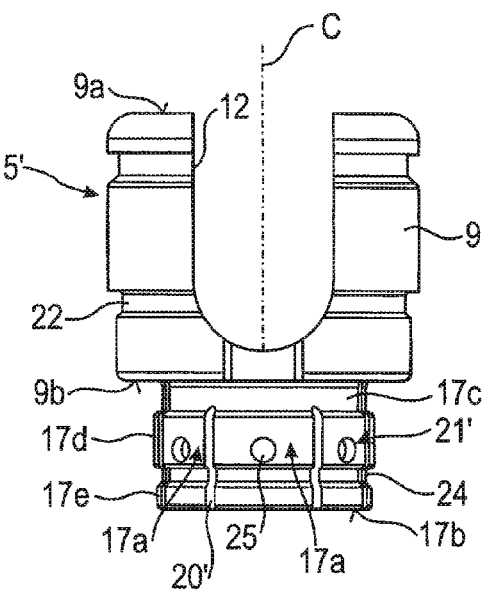
Figure 8C:
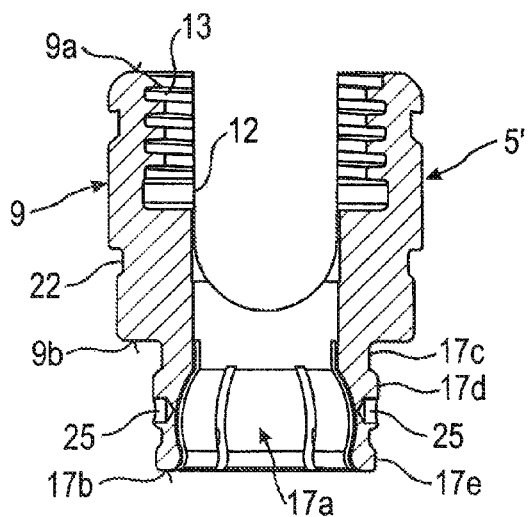
Figure 8D:
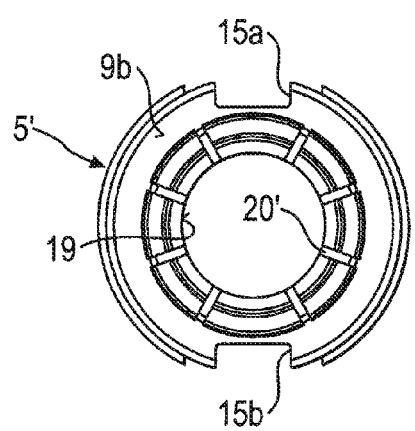
Figure 9A:
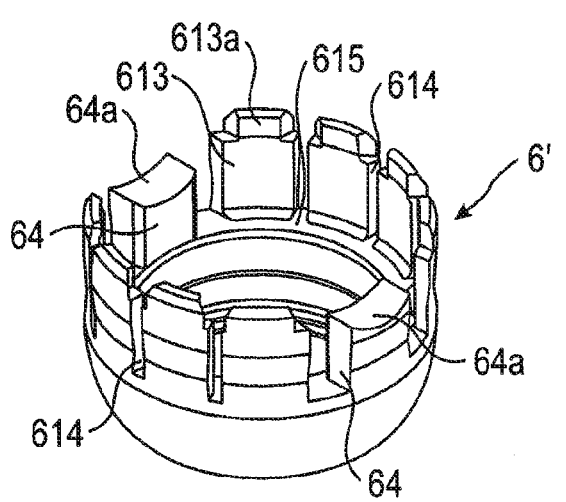
FIGS. 9a to 9d show a perspective view, a bottom view, a side view, and a cross-sectional view, respectively, of a locking ring of the bone anchoring device of the second embodiment.
Figure 9B:
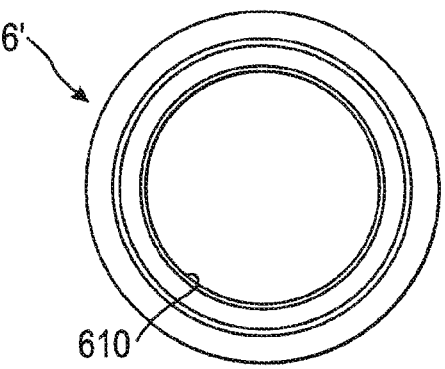
Figure 9C:
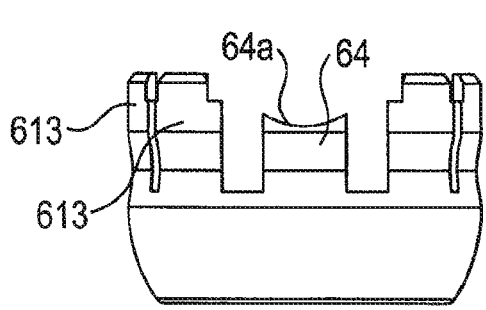
Figure 9D:
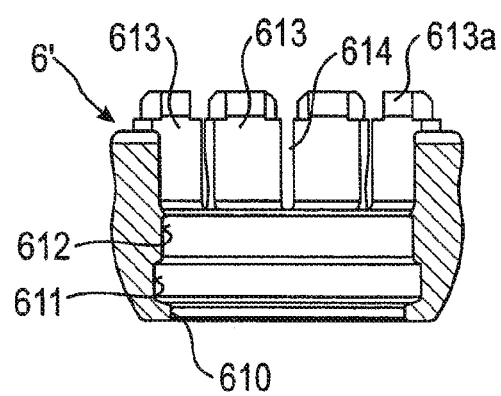

As can be seen in FIG. 5c, which shows a cross-sectional view of the bone anchoring device with inserted rod and tightened inner screw 7 in a cross-section containing the rod axis, the locking ring 6 does not engage the flexible wall section 17a other than at the distinct pressure areas corresponding to the teardrop-shaped projections 21. In other areas, there may be a gap between parallel surfaces of the inner cylindrical surface 61 and the flexible wall sections 17a. Hence, pressure is applied only at the distinct pressure areas, which are evenly distributed in a circumferential direction. Pressure is not exerted at positions which do not contribute to or which may otherwise contribute less to clamping the head 3, such as at or around the slits 20. Therefore, efficiency of applying the clamping force is increased or improved.

A second embodiment of the bone anchoring device will now be described with reference to FIGS. 6 to 10c. Parts and portions which are identical or similar to the parts and portions of the first embodiment are described by the same reference numerals, and the descriptions thereof will not be repeated. The bone anchoring device of the second embodiment differs from the bone anchoring device of the first embodiment in the designs of the pressure area and of the locking ring.

As can be seen in particular in FIGS. 6 and 8a to 8d, a receiving part body 5' has at its outer surface of a rod receiving portion 9 an engagement portion for a locking ring 6', in the form of a circumferential groove 22 and a cylindrical portion 23 with a slightly reduced diameter compared to a substantially cylindrical portion on an opposite side of the groove 22. The groove 22 acts as a stop for the locking ring 6' in a second position, which is a pre-locking position described below.

The head receiving portion 17 includes pressure areas which are realized by one or more ball bearings 21' provided in each flexible wall section 17a, respectively. The head receiving portion 17 has a first cylindrical section 17c adjacent to the second end 9b of the rod receiving portion 9 with a first diameter, and a second cylindrical portion 17d with a second diameter greater than the first diameter and which may include the ball bearings 21'. A third portion 17e with a diameter that may be essentially the same as that of the second portion 17d is provided at the free end 17b. Between the second portion 17d and the third portion 17e, a groove 24 may be provided that serves for engagement with a portion of the locking ring 6'. It shall be noted that the grooves 22 and 24 may each have an inclined lower edge which is inclined towards the free end 17b, to facilitate disengagement of the locking ring 6' when moving the locking ring 6' downwards. The second portion 17d is arranged substantially at a position around a largest diameter of the hollow internal section 18, which corresponds to a largest outer diameter of the head 3 when the head 3 is inserted into the hollow interior section 18. Slits 20' preferably extend from the free end 17b only as far as an upper end of the second portion 17d, as shown, for example, in FIGS. 8b and 8c.

Each of the flexible wall sections 17a includes a distinct pressure area in the form of a ball bearing 21' at its center in a circumferential direction. Each ball bearing assembly 21' may include a ball 26 and a recess 25 having a substantially circular cross section which is sized and shaped to accommodate the ball 26 therein. The ball 26 can rotate in the recess 25, where a portion of the ball 26 projects out of the second cylindrical portion 17d. After the locking ring 6' is mounted, the balls 26 cannot fall out of the recesses 25. As best seen in FIGS. 6 and 10a to 10c the receiving part body 5' includes in a circumferential direction equidistantly spaced balls 26 that cooperate with the locking ring 6'.

The locking ring 6' will now be described with respect to FIGS. 9a to 9d. The locking ring 6' is substantially cylindrical and has an upper end 6a and a lower end 6b. Near the lower end 6b, an inwardly projecting circular edge 610 is provided that is configured to cooperate with the third portion 17e adjacent the free end 17b of the head receiving portion 17. The inwardly projecting edge 610 provides a cylindrical inner surface. Furthermore, the inwardly projecting edge 610 is configured to engage the groove 24 of the head receiving portion 17.

Figure 10A:
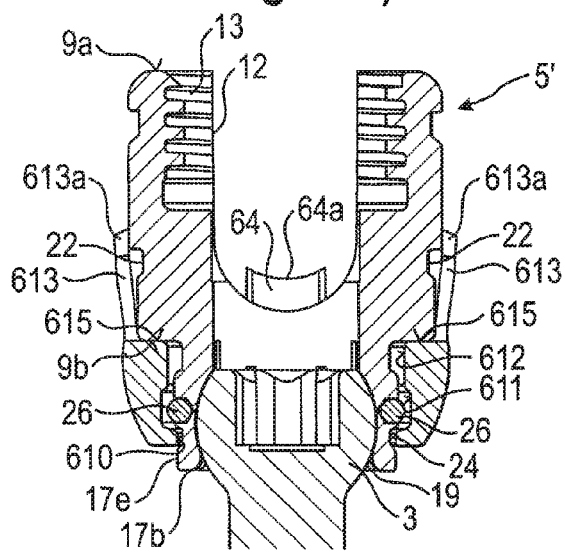
FIGS. 10a to 10c show cross-sectional views of steps of use of the bone anchoring device according to the second embodiment.
Figure 10B:
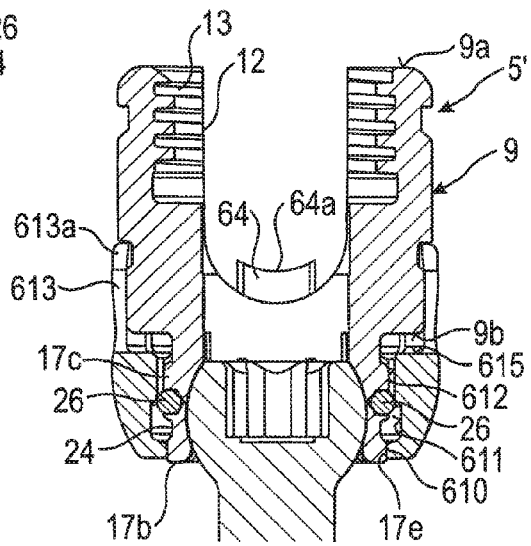

Adjacent the inwardly projecting edge 610, the locking ring 6' has a hollow cylindrical portion 611, a height of which is such that the hollow area can receive the portions of the balls 26 protruding out of the recesses 25, as can be seen in particular in FIG. 10a. Hence, an inner diameter of the portion 611 is larger than the inner diameter of the inwardly projecting edge 610. Adjacent the hollow cylindrical portion 611 on a side opposite the projecting edge 610, there is a hollow cylindrical portion 612, an inner diameter of which may be smaller than the inner diameter of the hollow cylindrical portion 611 and larger than the inner diameter of the inwardly projecting edge 610. The inner diameter of the hollow cylindrical portion 612 is such that, as can be seen in FIG. 10b when the locking ring 6' is around the head receiving portion 17 such that the hollow cylindrical portion 612 is positioned around the balls 26, the inner surface of the hollow cylindrical portion 612 can slide along the balls 26 of the ball bearings 21'.

An upper portion of the locking ring 6' adjacent to the upper end 6a includes upwardly extending wall portions 613, which are separated from each other by slits 614. The upwardly extending wall portions 613 are arranged at an outer circumference of an inner circumferential shoulder 615 of the locking ring 6', and render the upper portion of the locking ring 6' flexible. A number and size of the slits 614 and a thickness of the wall portions 613 are configured such that a desired flexibility is obtained. At their free ends the wall portions 613 include engagement sections 613a, which are shaped so as to engage the groove 22 provided on the outer surface of the rod receiving portion 9.

The locking ring 6' is sized in such a way with respect to the head receiving portion 17 that the head receiving portion 17 can expand within the locking ring 6' to allow the introduction of the head 3 when the locking ring 6' is in the first position as shown in FIG. 10a.

Two projections 64 which may each have a concave upper surface portion 64a are provided 180° offset from each other, like for the locking ring 6 of the first embodiment. A curvature of the upper surface 64a may correspond to a curvature of the rod 100. The projections 64 have a height such that they project above a bottom of the U-shaped recess 12 and extend into the cut-outs 15a, 15b when the locking ring 6' is in positions in which the head 3 is not yet locked, as shown in FIGS. 10a and 10b. The height of the upwardly extending wall portions 613 are such that, when the locking ring 6' is in a first position, as shown in FIG. 10a in which the inner circumferential shoulder 615 of the locking ring 6' abuts against the second end 9b of the rod receiving portion 9, portions of the upwardly extending wall portions 613 including the engagement portions 613a extend above the circumferential groove 22. On its outside, the locking ring 6' may be tapered towards its lower end 6b to reduce an outer dimension of the bone anchoring device.

The function and use of the bone anchoring device according to the second embodiment will now be explained with reference to FIGS. 10a to 10c. As shown in FIG. 10a, a first position of the locking ring 6', which is the insertion position in which the locking ring 6' is latched with respect to the receiving part body 5', is defined in such a way that the inwardly projecting edge 610 engages or is adjacent to the groove 24 at the outer surface of the head receiving portion 17. In this condition, the head 3 can be inserted through the opening 19 into the hollow internal section 18 of the head receiving portion 17. Since the inner diameter of the inwardly projecting edge 610 is larger than the outer diameter of the groove 24, an expansion of the head receiving portion 17 when the head 3 is introduced is possible. In the first position, the locking ring 6' may additionally be held by a clamping force between the rod receiving portion 9 and the flexible wall portions 613 of the locking ring 6', which may be bent slightly outwards, as can be seen in particular in FIG. 10a.

When the locking ring 6' is in the first position, the head receiving portion 17 is not compressed. In this position, the locking ring is prevented from moving further upwards towards the first end 9a of the rod receiving portion 9, since the locking ring 6' abuts with the shoulder 615 against the second end 9b of the rod receiving portion 9, and/or with the inwardly projecting edge 610 against an upper wall of the groove 24. This holds the locking ring 6' in place. The inclined lower edge of the groove 24 prevents an inadvertent downward movement of the locking ring 6', but allows for downward movement upon exertion of an additional downwardly directed force on the locking ring 6'. In the first position, the head 3 can freely pivot in the hollow internal section 18. The head receiving portion 17 is not compressed and the balls 26 may not be touched by the locking ring 6', since the balls 26 project into the hollow cylindrical portion 611.

A second position in which the locking ring 6' is latched with respect to the receiving part body 5' is shown in FIG. 10b. The second position is a pre-locking position in which the head 3 is prevented from removal from the hollow internal section 18 and optionally may be held in a preliminary angular position by a slight friction force exerted by the flexible wall sections 17a. In the second position, the locking ring 6' has been shifted towards the free end 17b of the head receiving portion 17 until the engagement portions 613a of the upwardly extending wall portions 613 resiliently snap into the groove 22 provided at the rod receiving portion 9. The free upper edge of the engagement portions 613a may abut against an upper wall of the groove 22, as shown in FIG. 10b, thereby preventing upward movement of the locking ring 6' out of the pre-locking position back towards the insertion position. On the other hand, the inclined lower edge of the groove 22 prevents an inadvertent downward movement of the locking ring 6' further towards the free end 17b, but allows such downward movement upon exertion of an additional axial force on the locking ring 6'.

To reach the second position from the first position, the locking ring 6' is shifted downwards. While the locking ring is shifted downwards, the hollow cylindrical portion 612 slides along the rotating balls 26, thereby exerting pressure onto the flexible wall section 17a at the positions of the balls 26. Hence, jamming between the two cylindrical surfaces 17d of the head receiving portion 17 and the hollow cylindrical portion 612 of the locking ring 6' is prevented or reduced, while simultaneously pressure is exerted onto the balls 26 which project out from the surface 17d. The balls 26 define distinct pressure areas to exert pressure onto the head 3 to clamp and eventually lock the head 3.

In the pre-locking position, the bone anchoring element 1 cannot be removed from the receiving part 5'. Hence, an accidental or inadvertent removal of the head 3 is not possible in this position. However, an angulation of the bone anchoring element 1 is still possible by overcoming a friction force between the head 3 and the receiving part 5', for example, manually.

Figure 10C:
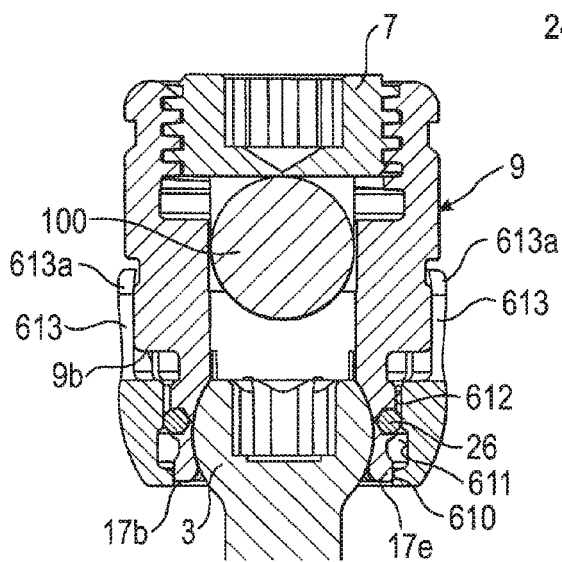
Figure 13A:
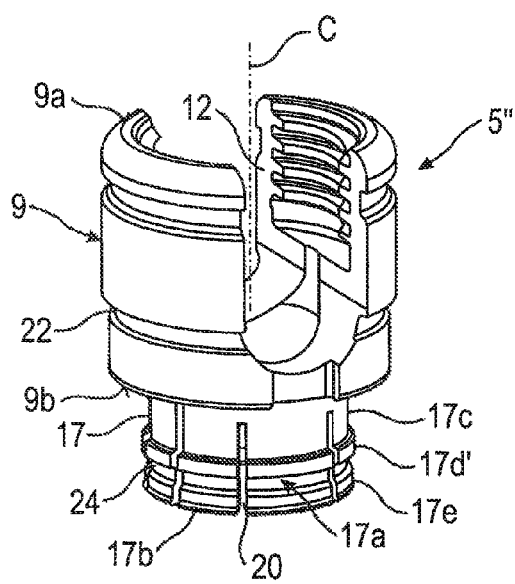
FIGS. 13a to 13d show a perspective view, a side view, a cross-sectional view, and a bottom view, respectively, of a receiving part body of the bone anchoring device according to the third embodiment.
Figure 13B:
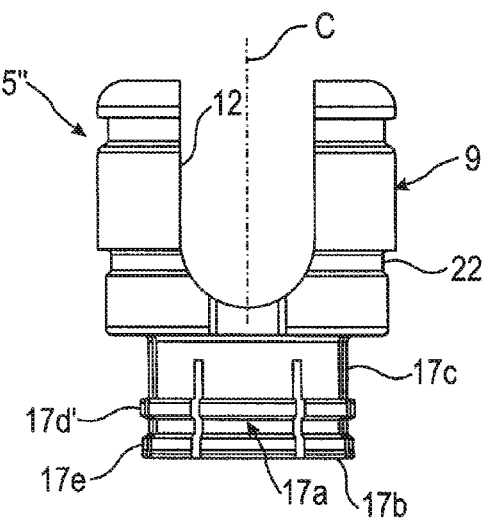
Figure 13C:
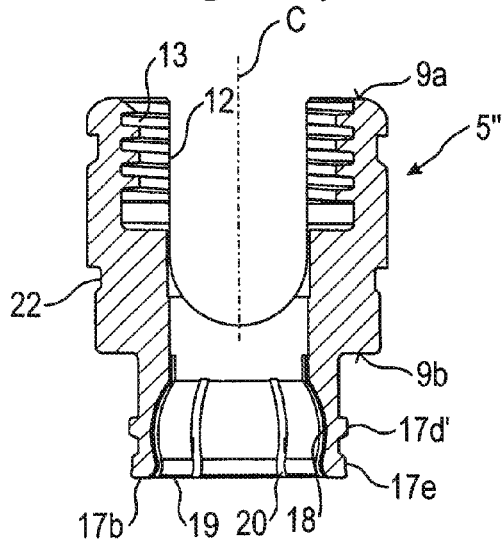
Figure 13D:
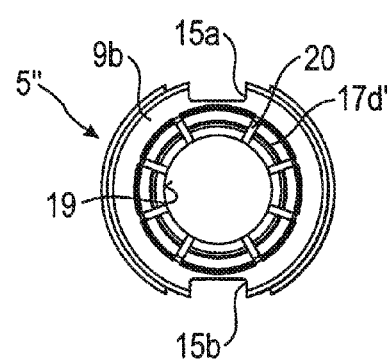

A third position, which is a locking position, is shown in FIG. 10c. The third position is defined as a position in which the head 3 is finally locked within the receiving portion 17. The inwardly projecting edge 610 compresses the third portion 17e adjacent the free end 17b of the head receiving portion 17 in this position. The combination of the pressure exerted via the pressure areas around the balls 26 and the pressure exerted via the inwardly projecting edge 610 firmly locks the head 3 within the receiving part body 5'. The third position is reached by a further downward movement of the locking ring 6' upon the action of the rod 100 pressing the upper surface 64a of the projections 64. The rod 100 is pressed downward when tightening the fixation screw 7.

A third embodiment of the bone anchoring device will now be described with reference to FIGS. 11 to 15c. Parts and portions which are the same or similar to those of the first and/or second embodiment are designated with same reference numerals and the descriptions thereof will not be repeated. The third embodiment of the bone anchoring device differs from the first and second embodiments in the designs of the pressure areas. In the third embodiment, pressure areas 21" are defined as circumferentially distinct projections which are located at an inner side of the locking ring 6" (see, e.g., FIG. 15c).

As can be seen in particular in FIGS. 13a to 13d, the receiving part body 5" has a head receiving portion 17 similar to the head receiving portion 17 of the second embodiment. A second cylindrical portion 17d' is provided at an axial position of the head receiving portion 17 which corresponds substantially to a largest outer diameter of the head 3 when the head 3 is inserted in the head receiving portion 17. The slits 20 extend similarly as in the first and second embodiments from the free end 17b to a distance from the second end 9b of rod receiving portion 9, and over the second cylindrical portion 17d'.

Figure 14A:
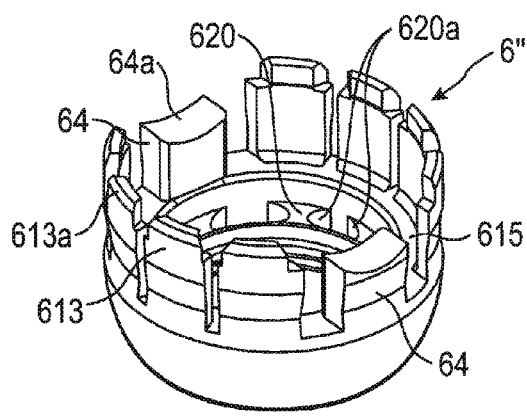
FIGS. 14a to 14d show a perspective view, a bottom view, a side view, and a cross-sectional view, respectively, of a locking ring of the bone anchoring device according to the third embodiment.
Figure 14B:
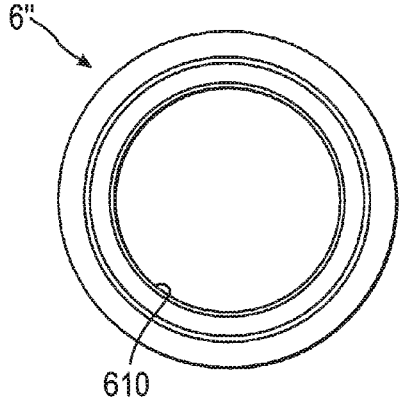
Figure 14C:
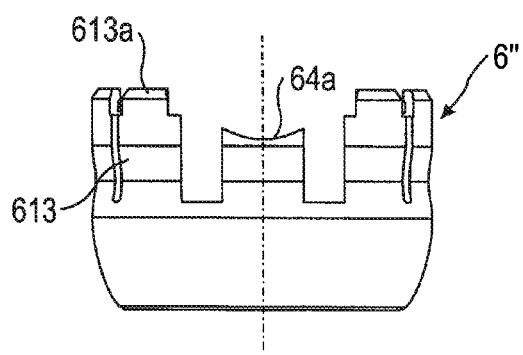
Figure 14D:
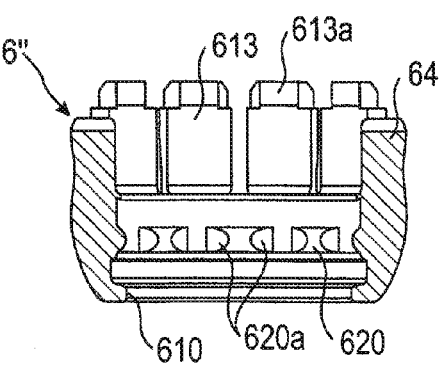

The locking ring 6" differs from the locking ring 6' according to the second embodiment in that the locking ring 6" has pressure areas in the form of circumferentially distinct projections 620 which are configured to be at an axial position corresponding to the position of the second cylindrical portion 17d' when the locking ring is in a third position as shown in FIG. 15c. The projections 620 project toward an inside of the locking ring 6". A number of projections 620 corresponds to a number of flexible wall segments 17a, and a distance between projections 620 corresponds to a distance, for example, between centers of the flexible wall sections 17a, so that when the locking ring 6" is mounted, each projection 620 can engage one flexible wall section 17a. The projections 620 have a height in an axial direction which is approximately the same as a height of the second cylindrical portion 17d'. The width of the projections 620 in a circumferential direction is smaller than a width of the flexible wall sections 17a, thereby creating distinct pressure areas for each flexible wall section 17a. The projections 620 can be generated by providing cutouts of a projecting ring with inclined cutting surfaces 620a, for example, as shown in FIG. 14a and FIG. 14d. However, other shapes may be possible to generate distinct pressure areas with respect to the flexible wall sections 17a.

Assembly and use of the bone anchoring device according to the third embodiment is similar to that of the second embodiment. As shown in FIG. 15a in a first position, an inwardly projecting edge 610 of the locking ring 6" engages a groove 24 at the head receiving portion 17. The head 3 can be introduced from the free end 17b when the locking ring 6" is in this position.

In a second position, which is a pre-locking position, as shown in FIG. 15b engagement portions 613a engage a groove 22 at a rod receiving portion 9 of the receiving part 5". In this position the projections 620 of the locking ring 6" may begin to press against the second cylindrical portion 17d' of the head receiving portion 17.

In the third position, as shown in FIG. 15c, the projections 620 are positioned substantially at the centers of the respective second cylindrical portions 17d' and compress the flexible wall sections 17a to clamp the head 3. In addition, the inwardly projecting edge 610 engages a third cylindrical portion 17e. The combination of pressure from the projections 620 and the inwardly projecting edge 610 causes the head 3 to be firmly locked within the hollow internal section 18.

Individual features from one of the embodiments described can be combined or exchanged with other features from other embodiments. For example, it is possible to have projections that form a distinct pressure areas on the flexible wall portions and on the locking ring alternately in a circumferential direction. The locking ring 6 and the receiving part 5 of the first embodiment can also be configured to have a pre-locking function, and alternatively, the locking rings and the receiving parts of the second and third embodiments can be designed without a pre-locking function.

Further modifications of the embodiments shown are also possible. For example, the head of the bone anchoring element can have various other shapes, such as, for example, a cylindrical shape, whereby a mono-axial bone screw is provided, allowing rotation of the bone anchoring element with respect to the receiving part body around a single axis.

The projections forming the pressure areas can have any shape. Preferably, they may have a rounded shape to facilitate movement of the locking ring.

The head receiving portion can have an inclined open end or can be otherwise asymmetric to allow a greater angulation of the head in one direction.

For the bone anchoring element, various different kinds of bone anchoring elements can be used and combined with the receiving part. These anchoring elements may include, for example, screws with different lengths, screws with different diameters, cannulated screws, screws with different thread forms, nails, hooks, anchoring elements where the head and the shaft are separate parts, etc.

The rod receiving portion may also have various different shapes. For example, the recess can be configured to allow the rod to be introduced from a side instead of being introduced from the top. The recess can also be closed instead of U-shaped. Various kinds of locking devices, including locking device with two or more parts, outer nuts, outer caps, bayonet locking devices, or various others types of locking devices may be utilized.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part for receiving a rod for coupling the rod to a bone anchoring element, the receiving part comprising:
a receiving part body with a first end, a second end, and a central axis extending from the first end to the second end, a rod receiving portion at the first end and having a channel for receiving a rod, and a head receiving portion at the second end for accommodating a head of a bone anchoring element, the head receiving portion having an open end for introducing the head; and
a locking ring configured to be positioned around the head receiving portion,
wherein the head receiving portion comprises a plurality of flexible wall portions, the flexible wall portions and the locking ring being configured to engage each other at circumferentially distinct pressure areas having positions corresponding to circumferentially separated projections on at least one of the flexible wall portions or the locking ring, and
wherein in a plane perpendicular to the central axis and including the pressure areas, a surface of the at least one of the flexible wall portions or the locking ring on which the projections are located is substantially circular with a center of curvature located on the central axis, and wherein at least one of the projections is formed by a curved portion having a center of curvature spaced apart from the central axis.

2. The receiving part of claim 1, wherein the flexible wall portions are separated by slits.

3. The receiving part of claim 1, wherein the projections are provided at the flexible wall portions.

4. The receiving part of claim 1, wherein the projections are provided at the locking ring.

5. The receiving part of claim 1, wherein the projections comprise wedge elements.

6. The receiving part of claim 1, wherein the projections are teardrop-shaped.

7. The receiving part of claim 6, wherein the teardrop-shaped projections are oriented such that widths and heights of the projections increase towards the open end.

8. The receiving part of claim 1, wherein the projections are ball-shaped.

9. The receiving part of claim 8, wherein the ball-shaped projections are formed by balls rotatably provided in corresponding recesses.

10. The receiving part of claim 1, wherein opposing surfaces of the head receiving portion and the locking ring in areas other than at the distinct pressure areas include portions that are parallel to one another when the locking ring is positioned around the head receiving portion.

11. The receiving part of claim 1, wherein the distinct pressure areas are configured to be positioned substantially at the center of each of the flexible wall portions.

12. The receiving part of claim 1, wherein the head receiving portion has a hollow internal section for accommodating the head, and wherein the distinct pressure areas are located along an axial direction of the receiving part body at positions corresponding to a largest inner diameter of the hollow internal section.

13. The receiving part of claim 1, wherein the locking ring can assume a second position relative to the receiving part body in which the locking ring is latched in a position in which a head of a bone anchoring element can be introduced into the head receiving portion, and a third position relative to the receiving part body in which the locking ring is latched in a position which prevents removal of an inserted head.

14. The receiving part of claim 1, wherein the locking ring further comprises an edge that projects towards a central axis of the locking ring at one end of the locking ring, the edge configured to cooperate with a portion of the head receiving portion near the open end to provide additional clamping of an inserted head.

15. The receiving part of claim 1, wherein at least one of the projections gradually tapers or curves towards or away from a corresponding central axis of the receiving part body or the locking ring along a circumferential direction.

16. The receiving part of claim 1, wherein when the flexible wall portions and the locking ring are engaged, the locking ring exerts a first force on at least one of the flexible wall portions at a corresponding pressure area, and exerts a second force less than the first force on the at least one flexible wall portion in a region circumferentially adjacent to the corresponding pressure area.

17. A bone anchoring device comprising:
a bone anchoring element having a shaft for anchoring in a bone and a head; and
a receiving part for receiving a rod for coupling the rod to the bone anchoring element, the receiving part comprising:
a receiving part body with a first end, a second end, and a central axis extending from the first end to the second end, a rod receiving portion at the first end and having a channel for receiving a rod, and a head receiving portion at the second end for accommodating the head, the head receiving portion having an open end for introducing the head; and
a locking ring configured to be positioned around the head receiving portion,
wherein the head receiving portion comprises a plurality of flexible wall portions, the flexible wall portions and the locking ring being configured to engage each other at circumferentially distinct pressure areas having positions corresponding to circumferentially separated projections on at least one of the flexible wall portions or the locking ring, and
wherein in a plane perpendicular to the central axis and including the pressure areas, a surface of the at least one of the flexible wall portions or the locking ring on which the projections are located is substantially circular with a center of curvature located on the central axis, and wherein at least one of the projections is formed by a curved portion having a center of curvature spaced apart from the central axis.

18. A method of coupling a rod to a bone or vertebra via a bone anchoring device, the bone anchoring device comprising an anchoring element having a shaft for anchoring in a bone or vertebra and a head, and a receiving part comprising a receiving part body with a first end, a second end, and a central axis extending from the first end to the second end, a rod receiving portion at the first end and having a channel for receiving a rod, and a head receiving portion at the second end for accommodating the head, the head receiving portion having a plurality of flexible wall portions and an open end for introducing the head, and a locking ring configured to be positioned around the head receiving portion, the method comprising:
inserting the bone anchoring device into a bone or vertebra;
adjusting an angular position of the receiving part relative to the bone anchoring element;
inserting a rod into the channel; and
advancing a closure element into the channel to push the rod against the locking ring and to move the locking ring towards the second end of the receiving part body to a locking position to lock the angular position of the receiving part relative to the bone anchoring element, wherein in the locking position, the locking ring engages the head receiving portion at circumferentially distinct pressure areas having positions corresponding to circumferentially separated projections on at least one of the flexible wall portions or the locking ring, and wherein in a plane perpendicular to the central axis and including the pressure areas, a surface of the at least one of the flexible wall portions or the locking ring on which the projections are located is substantially circular with a center of curvature located on the central axis, and wherein at least one of the projections is formed by a curved portion having a center of curvature spaced apart from the central axis.

19. The method of claim 18, wherein prior to inserting the bone anchoring device into the bone or vertebra, the method further comprises moving the locking ring from a second position to a third position relative to the receiving part body to prevent an inserted head inserted into the head receiving portion from being removed, wherein the locking ring is latched in the third position.

20. The method of claim 19, wherein when the locking ring is in the third position, the locking ring exerts a pressure on the head receiving portion to releasably hold the head at a temporary angular position relative to the receiving part.

21. The method of claim 19, wherein prior to moving the locking ring from the second position to the third position, the method further comprises inserting the head into the head receiving portion when the locking ring is latched in the second position and the head receiving portion remains expandable to facilitate insertion of the head.

* * * * *